US009107486B2

(12) United States Patent
Brewer et al.

(10) Patent No.: US 9,107,486 B2
(45) Date of Patent: Aug. 18, 2015

(54) EXFOLIATING BRUSH HEAD FOR A PERSONAL CARE APPLIANCE

(71) Applicant: L'Oreal, Paris (FR)

(72) Inventors: Gerald Keith Brewer, Redmond, WA (US); Kenneth A. Pilcher, Seattle, WA (US); Robert E. Akridge, Seattle, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/862,280

(22) Filed: Apr. 12, 2013

(65) Prior Publication Data

US 2014/0309662 A1 Oct. 16, 2014

(51) Int. Cl.

| | |
|---|---|
| ***A61B 17/50*** | (2006.01) |
| ***A45D 34/04*** | (2006.01) |
| ***A46B 9/02*** | (2006.01) |
| ***A46B 9/06*** | (2006.01) |
| ***A46B 13/00*** | (2006.01) |
| ***A46B 13/02*** | (2006.01) |
| ***A61H 7/00*** | (2006.01) |

(52) U.S. Cl.

CPC .............. *A45D 34/042* (2013.01); *A46B 9/021* (2013.01); *A46B 9/028* (2013.01); *A46B 9/06* (2013.01); *A46B 13/008* (2013.01); *A46B 13/02* (2013.01); *A61H 7/002* (2013.01); *A61H 7/005* (2013.01); *A46B 2200/102* (2013.01)

(58) Field of Classification Search

CPC ................... A61B 17/54; A61B 2017/320012; A61B 17/50; A61B 2017/00747

USPC ........................... 606/131, 133; 604/313, 289

See application file for complete search history.

(56) References Cited

U.S. PATENT DOCUMENTS

| | | | | |
|---|---|---|---|---|
| D524,441 | S | 7/2006 | Anderson | |
| 7,320,691 | B2 * | 1/2008 | Pilcher et al. | 606/131 |
| 7,386,906 | B2 | 6/2008 | Roth | |
| 7,581,545 | B1 | 9/2009 | Moldawski | |
| 7,786,626 | B2 | 8/2010 | Reishus | |

(Continued)

FOREIGN PATENT DOCUMENTS

| | | | |
|---|---|---|---|
| WO | 01/56529 | A2 | 8/2001 |
| WO | 2005/091748 | A2 | 10/2005 |

OTHER PUBLICATIONS

"SkinSpa, Sonic Exfoliator, 901 Spa, Silk-épil 7 Type 5377," product manual, Braun GmbH, Kronberg, Germany, <http://www.service.braun.com/product/product.asp?rg=EU&c=NO&I=GB&typ=ui&frmTyp=subgrp&grp=SH07%3C%7C%3E&s=&subgrp=Silk%20Epil%207,%20Silk%20Epil%20Xpressive&des=&sString=5377%7CSH%7CSH07%7CS%7CSilk%20Epil%207%20-%20Legs%20Body%20&seite=3> [retrieved Apr. 9, 2013], 89 pages.

(Continued)

*Primary Examiner* — Victor Nguyen

(74) *Attorney, Agent, or Firm* — Christensen O'Connor Johnson Kindness PLLC

(57) ABSTRACT

Exfoliating brush heads are disclosure for use with a personal care appliance. The personal care appliance is configured to oscillate the exfoliating brush head to provide improved smoothing and exfoliation of a patient's epidermis with or without the antecedent application of skin care formula. The oscillating action of the exfoliating brush head may be rotational, translational, or a combination thereof. In use, the personal care appliance oscillates the exfoliating brush head over a patient's skin in order to remove dead skin from the patient's epidermis. The exfoliating brush head may include first and second groups of tufts, wherein the first and second groups of tufts have different bristle heights and/or stiffness.

22 Claims, 7 Drawing Sheets

(56) References Cited

U.S. PATENT DOCUMENTS

| | | | |
|---|---|---|---|
| D623,801 | S | 9/2010 | Curran |
| 8,066,013 | B2 | 11/2011 | Tes |
| 2006/0137703 | A1 | 6/2006 | Kling |
| 2006/0178676 | A1 | 8/2006 | Anderson |
| 2007/0221238 | A1 | 9/2007 | Tran |
| 2012/0301210 | A1 | 11/2012 | Sturgis |
| 2013/0023805 | A1 | 1/2013 | Ungemach |
| 2013/0023806 | A1 | 1/2013 | Ungemach |

OTHER PUBLICATIONS

International Search Report and Written Opinion mailed Jul. 17, 2014, issued in corresponding International Application No. PCT/US2014/033687, filed Apr. 10, 2014, 11 pages.

* cited by examiner

EXFOLIATING BRUSH HEAD FOR A PERSONAL CARE APPLIANCE

BACKGROUND

As is well known to those skilled in the art, thick calluses or corns are typically formed on the palms of the hands or the soles of the feet when the epidermis of the palms or the soles becomes partially keratinized due to frequently repeated contact of the hands or feet with a variety of hard or coarse surfaces over time. For example, calluses on the hands are often caused by the regular handling of an object that puts pressure on the hand, such as tools or sports equipment. Calluses and corns on the feet are often caused by pressure from footwear such as tight shoes, high-heeled shoes, loose shoes, and thin-sole shoes. The repeated pressure due to contact causes the skin to die and form a hard, protective surface.

Calluses and corns can cause discomfort and can also become painful. Moreover, calluses or corns crack due to, for example, dry or cold weather, thus allowing the dermis under the epidermis to be damaged. Therefore, it is often necessary to periodically remove such calluses or corns from the palms of the hands or soles of the feet. Such removal of calluses or corns from the hands or feet is commonly called "a pedicure."

During a pedicure, calluses and dry, flaky skin are abraded or scraped from the bottom of the feet. Typically, the feet are soaked in a warm bath and/or a topical formula is applied to soften the skin. Once the warm water and/or a topical formula has softened the skin on the feet, the bottoms of the feet are manually scrubbed with either a pedicure sander comprised of an abrasive sanding pad attached to a durable plastic handle, a callus rasp, or a pumice stone. Additionally, some technicians will use a corn and callus plane comprised of a stainless steel head with a raised shaving blade to slice thick, tough callus from the feet.

These conventional methods and apparatuses for callus removal are time consuming, laborious, inefficient, and often painful. Additionally, some of the conventional instruments present hazards. In particular, a callus plane may cause serious injury if used improperly. Accordingly, to reduce the risks and deleterious effects of the manual process, attempts have been made to automate the process of removing skin imperfections from the feet and hands. For example, several electrically powered rotary devices with sandpaper-like contact surfaces have been devised for grooming hands and feet, one such device being sold under the brand name "Pedi-Smooth." However, improved devices for removing calluses and rough skin are still desired.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present disclosure, an exfoliating brush head is provided for treating skin of a patient's epidermis. The exfoliating brush head includes a brush body configured to be mountable to a drive system configurable to impart motion to the brush body. The exfoliating brush head also includes a first group of tufts, wherein each tuft comprises a plurality of bristles outwardly extending from the brush body. In some embodiments, the tufts of the first group are configured to apply a non-Newtonian fluid to areas of rough skin of a patient's epidermis. The exfoliating brush head further includes a second group of tufts, wherein each tuft comprises a plurality of bristles outwardly extending from the brush body. In some embodiments, the second group of tufts is configured to exfoliate the areas of rough skin of a patient's epidermis when placed in contact therewith.

In accordance with another aspect of the present disclosure, an exfoliating brush head is provided for treating a patient's epidermis. The exfoliating brush head includes a brush body configured to be mountable to a drive system configurable to impart oscillating movement to the brush body, a first group of tufts, each tuft comprising a plurality of bristles outwardly extending from the brush body, and a second group of tufts configured to exfoliate a partially keratinized area of skin, each tuft comprising a plurality of bristles outwardly extending from the brush body. In some embodiments, the tufts of the second group of tufts are stiffer than the tufts of the first group.

In accordance with yet another aspect of the present application, a method is provided for exfoliating skin from a patient's epidermis. The method includes oscillating, via a motorized drive system, an exfoliating brush head having a first group of tufts and a second group of tufts. In some embodiments, the second group of tufts are configured to exfoliate partially keratinized areas of the patient's epidermis. The method also includes applying the second group of tufts against partially keratinized areas of the patient's epidermis.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

Figure 1:
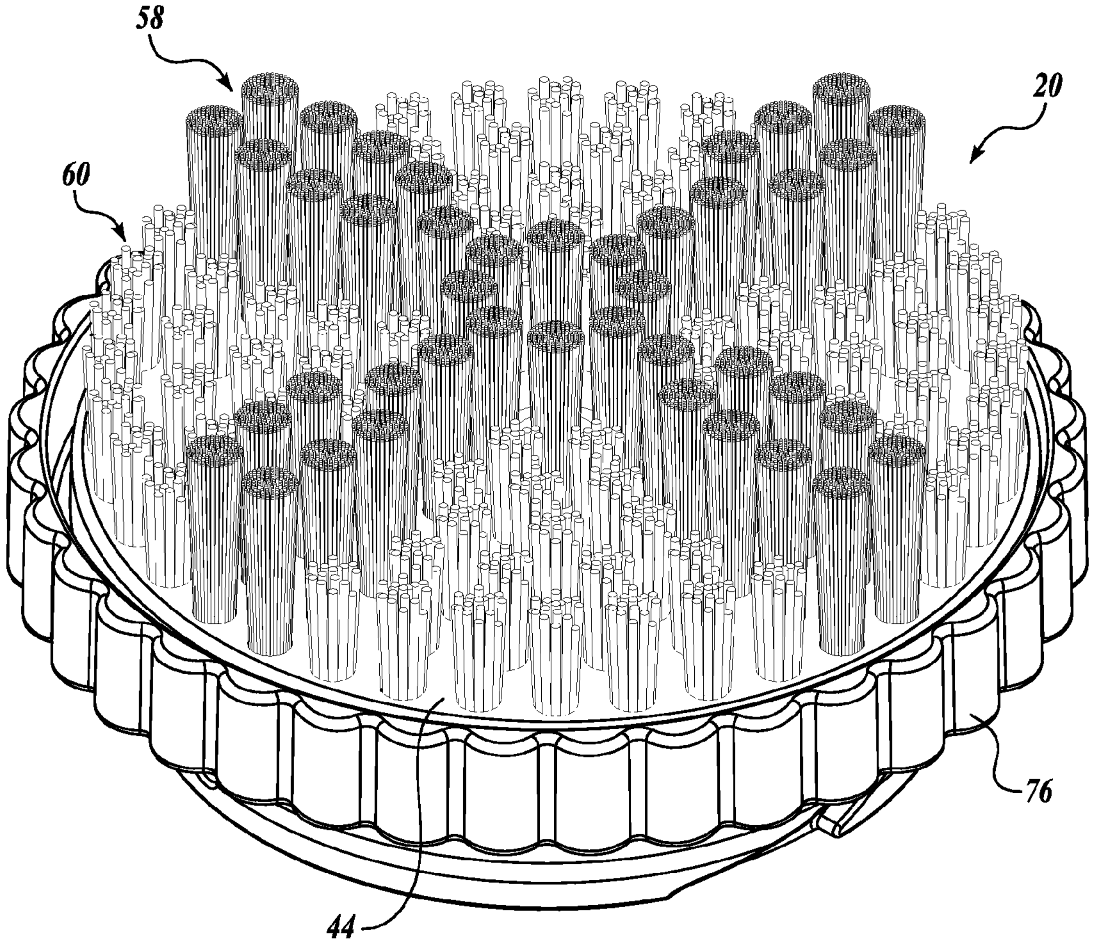
FIG. 1 is a perspective view of one example of an exfoliating brush head in accordance with aspects of the present disclosure.

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The following discussion provides examples of systems, apparatuses, and/or methods for exfoliating skin. The examples described herein provide exfoliating brush heads suitable for use with a personal care appliance. In some examples described herein, the personal care appliance oscillates the exfoliating brush head to provide improved smoothing and exfoliation of a patient's epidermis with the antecedent application of a fluid for softening skin, such as a skin care formula. In other examples described herein, the personal care appliance oscillates the exfoliating brush head to provide improved smoothing and exfoliation of a patient's epidermis without the antecedent application of skin care formula.

In the examples set forth herein, the oscillating action of the exfoliating brush head may be rotational, translational, or a combination thereof. In use, the personal care appliance oscillates the exfoliating brush head over a patient's skin in order to remove dead skin from the patient's epidermis. In some embodiments, the exfoliating brush head includes first and second groups of tufts, wherein the first and second groups of tufts have different bristle heights and/or stiffness. In these examples and others, the tufts of the first group are more pliant than the tufts of the second group, and are configured to sufficiently deliver and apply a non-Newtonian fluid, such as a skin care formula, to the skin to be treated. In other examples, the tufts of the second group are configured to sufficiently treat rough skin conditions, such as calluses or corns, which have developed on a patient's hand or foot. As used herein, the term "rough skin" means skin of the epidermis that has partially keratinized, and includes the skin conditions referred to as corns and calluses.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Turning now to FIG. 1, there is shown one example of an exfoliating brush head, generally designated 20, formed in accordance with aspects of the present disclosure. The brush head 20 is suitable for use with a personal care appliance, such as appliance 22, illustrated in FIGS. 6 and 7. The brush head 20 in some embodiments includes a first group of tufts 58 that can be oscillated over a patient's skin in order to apply, for example, a skin softening fluid, to rough skin of the epidermis, and a second group of tufts 60 that can be oscillated over the rough skin in order to treat the rough skin of the epidermis. As will be described in more detail below, some embodiments utilize sonic motion for oscillating the brush head 20, which can provide improved control and precision for sculpting skin and/or callus/corn removal.

Prior to describing the brush head 20 in more detail, one example of a personal care appliance 22 that may be employed to impart an oscillating motion to the brush head 20 will be described in some detail. While the personal care appliance 22 is one type of appliance that can be practiced with embodiments of the present disclosure, it will be appreciated that the brush head 20 is suitable for use with a wide range of oscillatory or vibratory motion generating devices.

Figure 7:
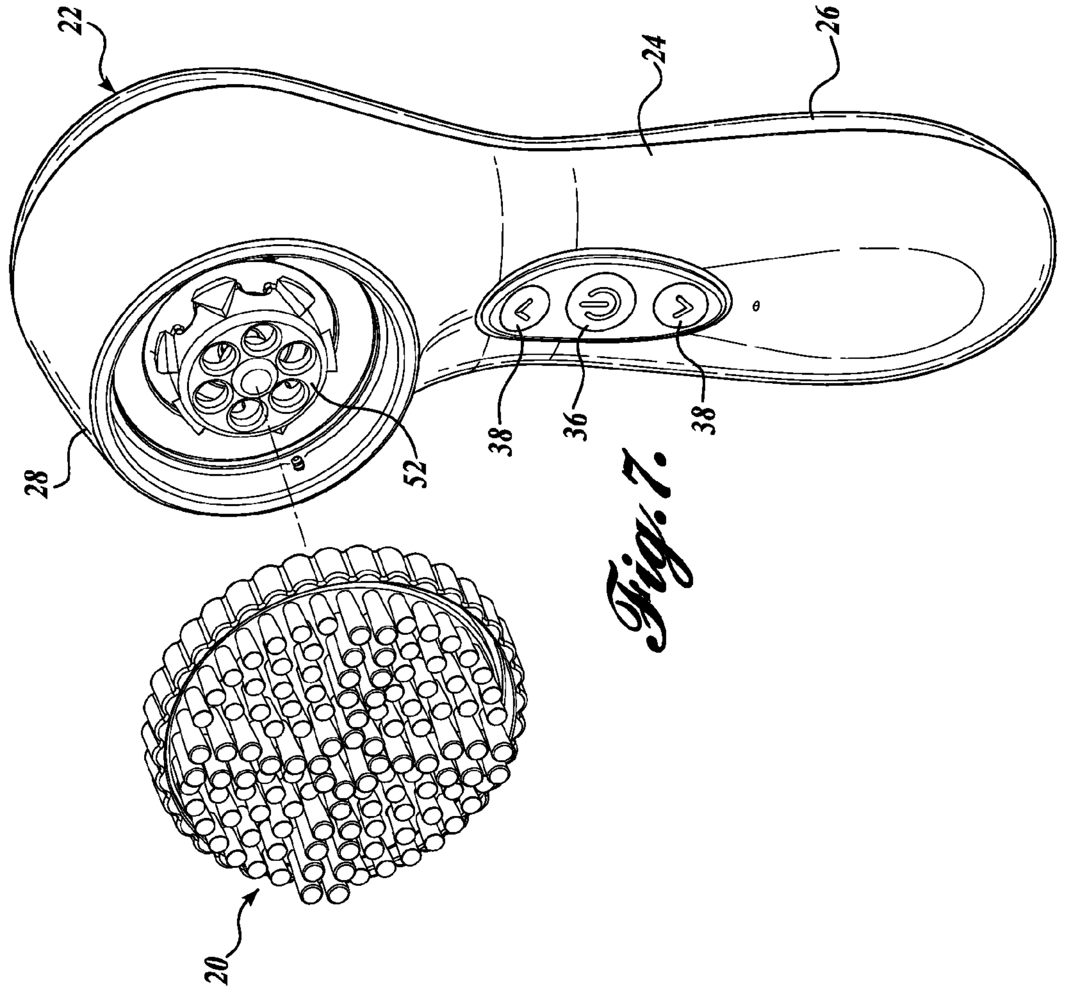
FIG. 7 is a perspective view of the personal care appliance of FIG. 8 with the exfoliating brush head exploded therefrom.
Figure 6:
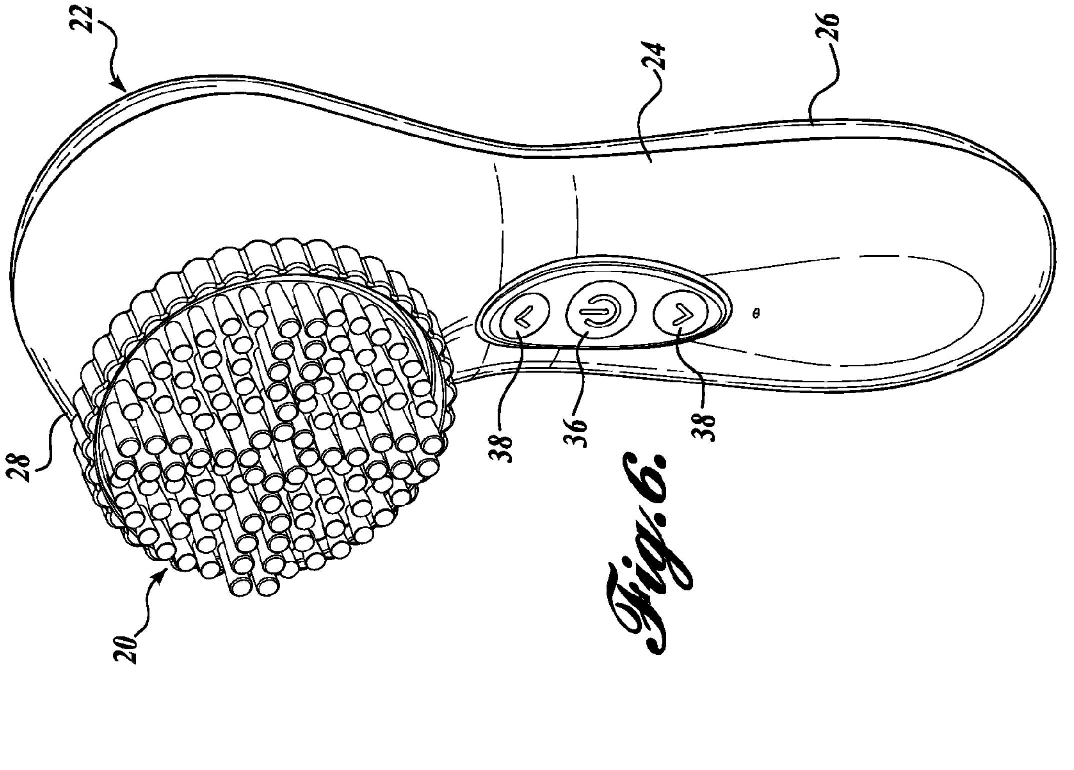
FIG. 6 is a perspective view of one example of a personal care appliance on which the exfoliating brush head of FIG. 1 is mounted.
Figure 8:
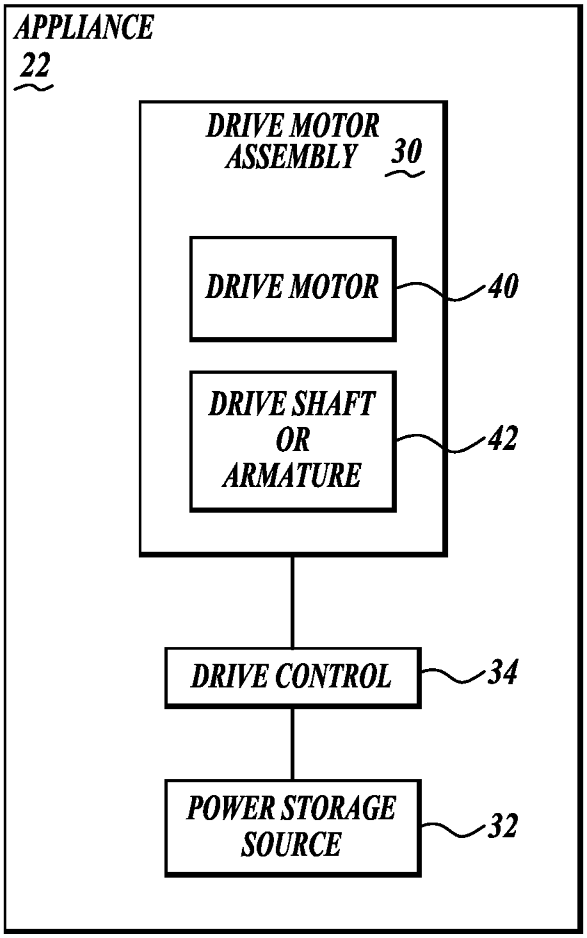
FIG. 8 is a functional block diagram of several components of the personal care appliance of FIG. 6.

Turning now to FIGS. 6 and 7, there is shown one example of the personal care appliance 22. The appliance 22 includes a body 24 having a handle portion 26 and a head attachment portion 28. The head attachment portion 28 is configured to selective attach a head, such as exfoliating brush head 20, to the appliance 22. The appliance body 24 houses the operating structure of the appliance. As shown in block diagrammatic form in FIG. 8, the operating structure in one embodiment includes a drive motor assembly 30, a power storage source 32, such as a rechargeable battery, and a drive control 34 that includes an on/off button 36 (See FIG. 6) configured and arranged to selectively deliver power from the power storage source 32 to the drive motor assembly 30. In some embodiments, the drive control 34 may also include a power adjust or mode control buttons 38 (See FIG. 6) coupled to control circuitry, such as a programmed microcontroller or processor, which is configured to control the delivery of power to the drive motor assembly 30. The drive motor assembly 30 in some embodiments includes an electric drive motor 40 that drives an attached head, such as exfoliating head 20, via a drive shaft or armature 42.

When the exfoliating brush head 20 is mounted to the head attachment portion 28, the drive motor assembly 30 is configured to impart motion to the brush head 20. The drive motor assembly 30 may be configured to operate the exfoliating brush head 20 at sonic frequencies, typically in the range of 80-160 Hz, oscillating the exfoliating brush head 20 back and forth within a range or amplitude of 3-20 degrees. In some embodiments, as will be described in more detail below, the exfoliating brush head 20 is operated in loaded or unloaded conditions at frequencies from about 80 Hz to 120 Hz with a range of about 3-17 degrees. In other embodiments, the exfoliating brush head 20 is operated in a loaded condition at frequencies from about 94 Hz to 106 Hz, a range or amplitude of 8-12 degrees, and a duty cycle of about 38-44%.

One example of a drive motor assembly 30 that may be employed by the appliance 22 to oscillate the exfoliating brush head 20 is shown and described in U.S. Pat. No. 7,786,626, the disclosure of which is hereby incorporated by reference in its entirety. However, it should be understood that this is merely an example of the structure and operation of one such appliance and that the structure, operation frequency and oscillation amplitude of such an appliance could be varied, depending in part on its intended application and/or characteristics of the exfoliating brush head, such as its inertial properties, etc. In some embodiments of the present disclosure, the frequency ranges are selected so as to drive the attached head at near resonance. Thus, selected frequency ranges are dependent, in part, on the inertial properties of the attached head. It will be appreciated that driving the attached head at near resonance provides many benefits, including the ability to drive the attached head at suitable amplitudes in loaded conditions (e.g. when contacting the skin). For a more detailed discussion on the design parameters of the appliance, please see U.S. Pat. No. 7,786,626.

Figure 2:
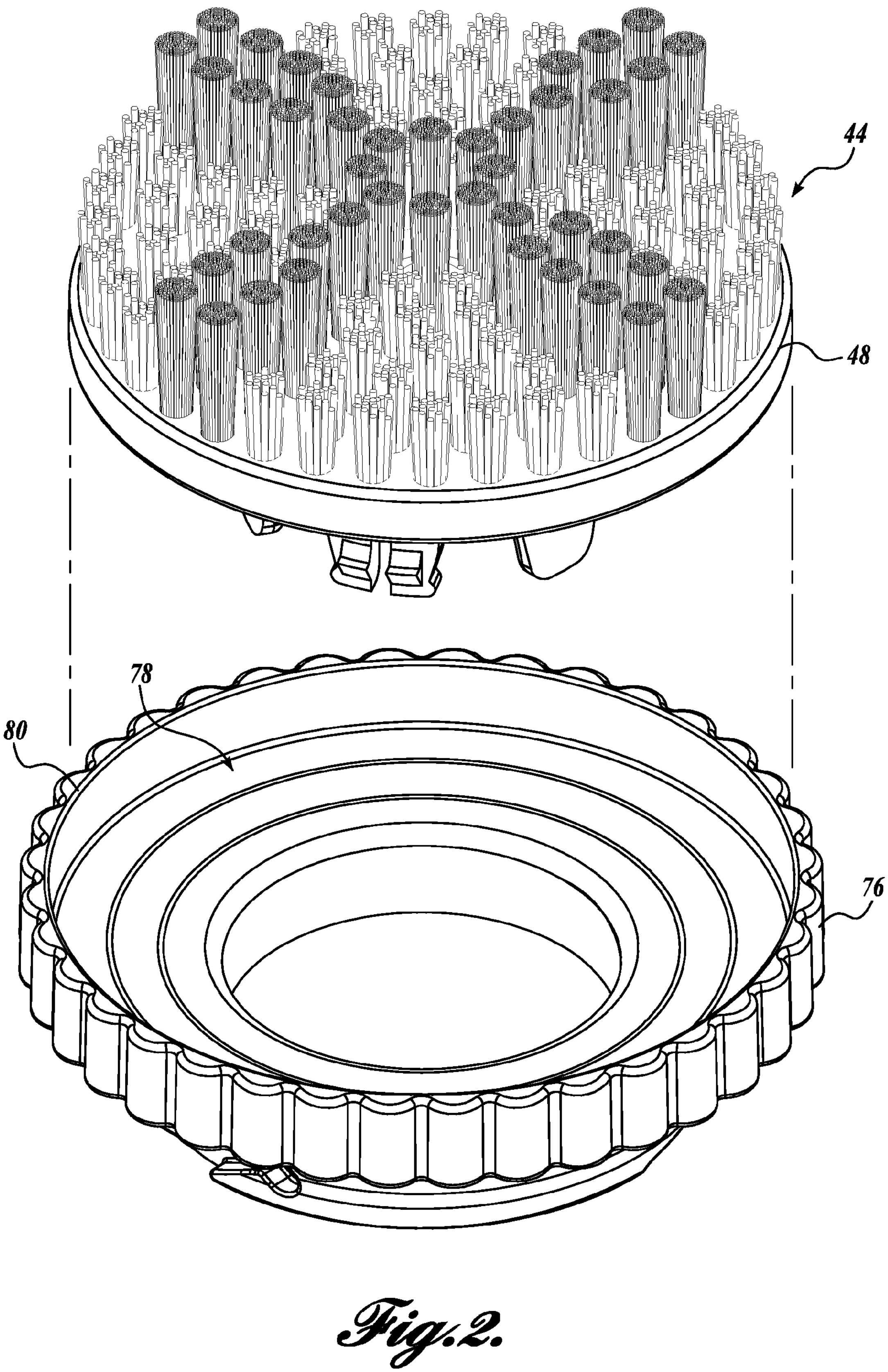
FIG. 2 is an exploded view of the exfoliating brush head of FIG. 1.
Figure 3:
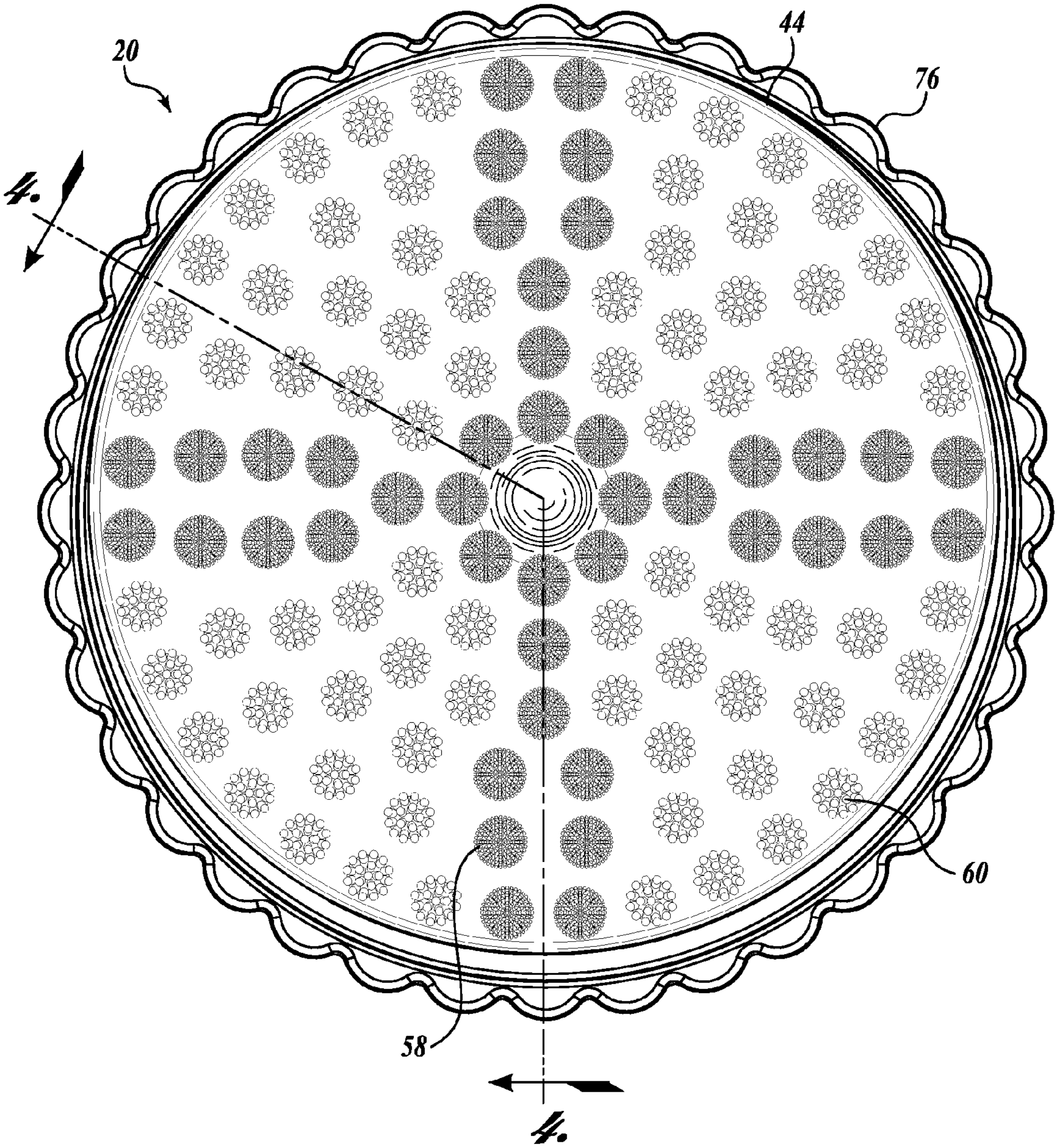
FIG. 3 is a top view of an exfoliating brush head, such as the exfoliating head of FIG. 1.
Figure 4:
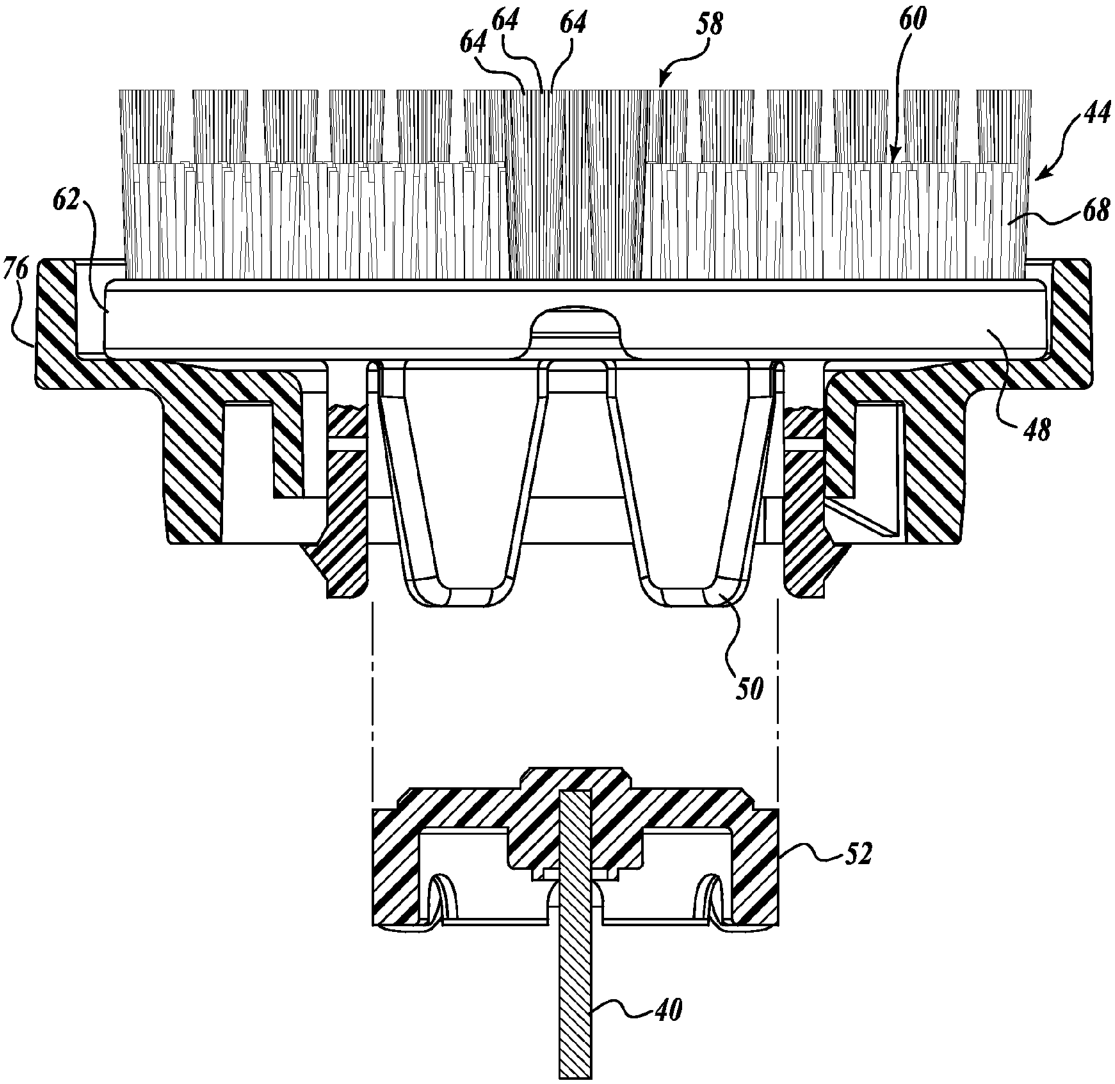
FIG. 4 is a cross-sectional view of the exfoliating brush head of FIG. 1 adapted to be coupled to components of a drive motor system.

Turning now to FIGS. 2-5, one example of the exfoliating brush head 20 will be described in more detail. As best shown in FIGS. 2 and 4, the brush head 20 includes a movable central portion 44. The movable central portion 44 includes a generally cylindrical body 48 configured to interface directly or indirectly with the drive shaft or armature 42 of the drive motor assembly 30 at a first or inner end 50. The body 48 is shown in FIG. 4 as being constructed out of plastic, such as nylon, polypropylene, polyurethane, polyethylene, etc., although other materials may be utilized, including lightweight metals, such as aluminum, titanium, etc.

The movable central portion 44 further includes first and second groups of tufts 58 and 60 disposed at an opposite, second or outer end 62. The tufts 58 of the first group are spaced apart from one another and include a plurality (e.g., 120-180) of bristles 64. The tufts 60 are spaced apart from one another and from the tufts 58 of the first group, and include a plurality (e.g., 12-24) of bristles 68. The bristles 64 and 68 extend upwardly from the outer surface of the body 48.

Generally described, the tufts 58 of the first group are configured to deliver a non-Newtonian fluid, such as a skin care formula, to the patient's skin and to spread the formula thereon. A non-Newtonian fluid, sometimes referred to as a thixotropic material, is a visco-elastic shear-thinning fluid with a Yield stress. In some embodiments, the skin care formula, which is capable of softening the epidermis, etc., has a Yield stress in the range of, for example, 50-140 Pa. The tufts 58 of the first group may also provide massaging or cleansing to the skin. In this regard, the bristles 64 of the tufts 58 of the first group in some embodiments have a height of about 0.360 inches (9.144 millimeters) to 0.400 inches (10.160 millimeters) or greater and a diameter in the range of about 0.003 inches (0.0762 millimeters) to 0.006 inches (0.152 millimeters). Additionally, each tuft can be formed with about 120-180 bristles 64. The bristles 64 can be constructed out of a variety of materials, such as polymers and co-polymers. In some embodiments, the bristles 64 may be constructed out of polybutylene terephthalate (PBT), polyethylene terephthalate (PET), nylon, polyester, a thermoplastic elastomer (TPE), combinations thereof, etc. In the embodiment shown, the height of the bristles 64 is generally constant.

It will be appreciated that the bristle and tuft characteristics (e.g., height, diameter, material type, bristle count, etc.) of the first group may be varied in embodiments of the present disclosure in order to configure the tufts 58 to be capable of delivering and applying a non-Newtonian fluid a subject's skin as the exfoliating head 20 is oscillating, for example, at the frequencies described above. In one exemplary embodiment of an exfoliating brush head formed in accordance with the disclosure, each tuft 58 includes 144 bristles constructed out of PBT and having a diameter of 0.004 inches (0.102 millimeters) and a height of 0.36 inches (9.144 millimeters). The exemplary brush head, as well as other examples, maintain skin care formula at or near the tips of the bristles 68 for easy transfer of the formula to the calloused skin of a subject.

Figure 5:
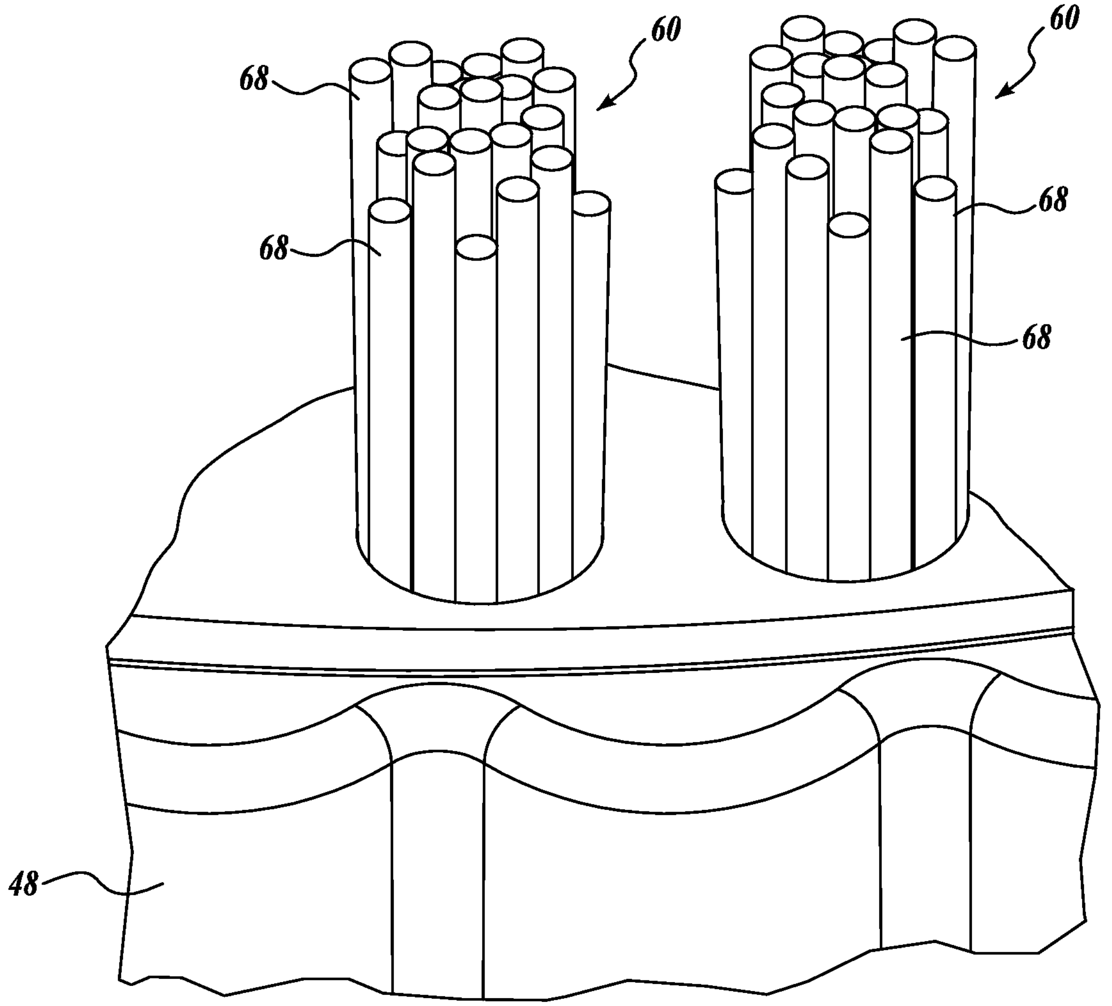
FIG. 5 is a partial enlarged view of a portion of exfoliating brush head of FIG. 1.

On the other hand, the tufts 60 of the second group are configured to exfoliate dead skin from the patient's epidermis, and in some embodiments, are configured to treat rough skin of the patient's epidermis where, for example, calluses and/or corns have developed. In this regard, the bristles 68 of the tufts 60 of the second group in some embodiments have a height of about 0.225 inches (5.715 millimeters) to 0.325 inches (8.255 millimeters) and a diameter of about 0.008 inches (0.2032 millimeters) to 0.020 inches (5.080 millimeters) or greater. Additionally, each tuft 60 can be formed with about 12-24 bristles 68. The bristles 68 can be constructed out of a variety of materials, such as polymers and co-polymers. In some embodiments, the bristles 68 may be constructed out of polybutylene terephthalate (PBT), polyethylene terephthalate (PET), nylon, polyester, a thermoplastic elastomer (TPE), combinations thereof, etc. In the embodiment shown, the height of the bristles 68 can vary, such as within the range stated above, within each tuft 60, as shown in FIG. 5. Slight variation in bristle heights of the bristles 68 can enhance the exfoliation of dead skin from the epidermis. In some embodiments of the present disclosure, tufts 60 can be deflected approximately 0.60 inches (15.240 millimeters) when a force of about 19 grams or greater is applied.

In will be appreciated that the bristle and tuft characteristics (e.g., height, diameter, material type, bristle count, etc.) of the second group may be varied in embodiments of the present disclosure in order to configure the tufts 60 to be capable of exfoliating partially keratinized areas, such as corns or calluses, on a subject's skin as the exfoliating head 20 is oscillating, for example, at the frequencies described above. In one exemplary embodiment of an exfoliating brush head formed in accordance with the disclosure, each tuft 60 includes 18 bristles constructed out of PBT and having a diameter of about 0.012 inches (3.048 millimeters) and a height of 0.325 inches (8.255 millimeters). The exemplary brush head, as well as other examples, easily sculpts and treats (e.g., reduces or removes) partially keratinized areas, such as corns or calluses, on a subject's skin.

Thus, the bristles 64 of the tufts 58 of the first group are more pliant (i.e., less stiff) than the bristles 68 of the tufts 60 of the second group. As a result, the tufts 60 of the second group are stiffer than the tufts 58 of the first group. Also, the bristles 64 of the tufts 58 of the first group extend farther from the body 48 than the bristles 68 of the tufts 60 of the second group. While contributing to the bristles 64 being more pliant than the bristles 68, the longer bristles 64 aid in the application of the skin care formula to the exfoliating brush 20 and/or the application of the skin care formula to the subject's skin.

In some embodiments, the bristles 64 and/or 68 are generally circular in cross-section, although the cross-sections of the bristles may vary, including square cross sections, X-shaped cross sections, etc. Additionally, the bristles 64 and/or 68 in some embodiments are formed without rounded ends. Further, the bristles 64 and/or 68 may be treated with anti-microbial agents in some embodiments or coated with an anti-microbial material, such as silver zeolites, zinc, copper, gold, etc. In other embodiments, the use of silver zeolite may be compounded into the resin that is used to construct the bristles 64 and/or 68 to reduce the bacterial and fungal effects on the bristles.

It will be appreciated that in some embodiments, the first 58 and second 60 tufts 58 and 60 can be arranged in random fashion while in other embodiments the first and second tufts 58 and 60 can be arranged in one or more patterns. In these embodiments, the one or more patterns can be constant throughout the majority of the surface or can vary throughout the majority of the surface 48 or parts thereof. In the embodiment shown, the first group of tufts 58 are arranged in an "X" shaped pattern, and the second group of tufts 60 are arranged in the four (4) quadrants created by the first group of tufts 58.

Returning to FIG. 2-4, the brush head 20 further includes an optional outer retainer 76. The outer retainer 76 includes a central, cylindrically shaped opening 78. The opening 78 is sized and configured to surround the sides of the movable central portion 44. When attached to the appliance 22, a rim 80, which extends around the top periphery of the central opening 78, is flush with or positioned slightly above the outwardly facing surface of the body 48.

In some embodiments, the central portion 44 and the outer retainer 76 together include an attachment system configured to provide selective attachment of the brush head 20 to the head attachment portion 28 of the personal care appliance 22. When attached to the personal care appliance 22 by the attachment system, the following occurs: (1) the movable central portion 44 is operatively connected to the drive motor assembly 30, for example, via a drive boss 52, in a manner that provides oscillating motion thereto; and (2) the outer retainer 76 fixedly secures the brush head 20 to the head attachment portion 28 of the appliance 22. Accordingly, the attachment system in some embodiments provides a quick and easy technique for attaching and detaching the brush head 20 to the personal care appliance 22. It will be appreciated that the attachment system also allows for other personal care heads to be attached to the appliance, and allows for replacement exfoliating brush heads 20 to be attached to the appliance, when desired.

One attachment system that may be practiced with embodiments of the present disclosure is set forth in U.S. Pat. No. 7,386,906, the disclosure of which is hereby incorporated by reference in its entirety. It will be appreciated that other attachment systems can be employed to provide either tooled or tool-less techniques for selectively attaching the brush head 20 to a personal care appliance, such as appliance 22, in a manner that (1) provides oscillating motion to the central portion 44; and (2) maintains the connection between the central portion 44 and the drive motor assembly 30. For example, in some embodiments, the central portion 44 includes a coupling interface configured to cooperatingly connect to an oscillating drive shaft or armature, such as armature 42, of an associated drive motor assembly 30 in a manner that transmits oscillating motion to the central portion 44 while fixedly securing the central portion 40 thereto. As such, it should be understood that while the retainer 76 may provide certain benefits to some embodiments of the brush head 20, it is optional, and thus, it may be omitted, if desired.

The above-described examples of the exfoliating brush head 20 can be used to exfoliate skin of a patient's epidermis. In that regard, the exfoliating brush head 20 is first attached to the personal care appliance 22. Next, if desired, a skin softening agent, such as skin care formula, can be placed on the tips of bristles 64 of the first group of tufts 58.

The personal care appliance 22 is then turned on and the exfoliating brush head 20 is operated at sonic frequencies in the range of about 80-120 Hz, oscillating the exfoliating brush head 20 back and forth within a range of about 3-17 degrees. In some embodiments, the exfoliating brush head 20 is operated in a loaded condition at frequencies of about 94 Hz to 106 Hz, with an amplitude or range of about 8-12 degrees, and a duty cycle of about 38-44%.

Once oscillating, the exfoliating brush head 20 is applied against the rough areas of skin on the body, such as on the feet or hands, in order to apply and spread the skin care formula. Because of the configuration of the bristles 64 of the first group of tufts 58, the skin care formula can be held at or near the bristle tips, thereby providing easy transfer and delivery of the skin care formula to the skin. The second group of tufts 60 can also be utilized to spread the skin care formula once applied to the skin. To do so, slight additional pressure is applied to the appliance 22 towards the skin. The second group of tufts 60 can also help to work the formula into the skin.

Once the skin formula has been spread on the skin, and sufficient time, for example, has elapsed in order to allow some softening of the skin, the exfoliating brush head 20 is reapplied against the rough areas of skin with slightly more pressure. With the added pressure applied to the appliance 22, the more pliant first group of tufts 58 yields so that the stiffer, second group of tufts 60 contact the rough skin. The exfoliating brush head 20 is then moved over the rough skin as the head 20 oscillates in order to reduce or remove the corn or callus from the epidermis.

The action of the second group of tufts 60, operated at the above amplitudes and frequencies, provide an exfoliating effect, thereby sculpting the rough areas of the skin and the removal or reduction of corns, calluses, etc. Once the skin is treated to the desired amount, the exfoliating brush head 20 can be removed from the skin and the appliance 22 can be powered down. Alternatively, the appliance 22 can be powered down automatically via a programmed operation.

Thus, using the exfoliating brush head 20 as described above, in the specified frequency and amplitude ranges, in the representative process outlined above, results in improved control and precision for skin sculpting and callus/corn removal. Additional benefits may also be realized by the exfoliating brush head 20 when used with a personal care appliance, such as appliance 22. For example, since skin can be removed with each directional change of the brush head 20 as a result of the oscillating motion imparted thereon, more skin can be removed with less force as compared to conventional rotary powered devices or manually powered devices.

The methods described above can be carried out without the use of skin care formulas or soaking of the skin in warm water in an attempt to soften the skin. However, any preparation of the skin area prior to exfoliation can be used as part of the method disclosed above.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. An exfoliating brush head for treating a patient's epidermis, comprising:

a brush body configured to be mountable to a drive system configurable to impart oscillating movement to the brush body;

a first group of tufts, each tuft comprising a plurality of first bristles outwardly extending from the brush body; and a second group of tufts configured to exfoliate a partially keratinized area of skin, each tuft comprising a plurality of second bristles outwardly extending from the brush body, wherein each bristle of the tufts of the second group of tufts extends from the brush body between about 0.225 inches to about 0.325 inches and has a diameter greater than about 0.008 inches;

wherein the tufts of the second group of tufts are stiffer than the tufts of the first group.

2. The exfoliating brush head of claim 1, wherein the first group of tufts is configured to deliver a non-Newtonian fluid to the partially keratinized area of skin.

3. The exfoliating brush head of claim 1, wherein the non-Newtonian fluid is a formula configured to soften the partially keratinized area of skin.

4. The exfoliating brush head of claim 3, wherein the non-Newtonian fluid includes a Yield stress in the range of 50-140 Pa.

5. The exfoliating brush head of claim 1, wherein the first bristles extend from the brush body about 0.360 inches to about 0.400 inches, and have a diameter of about 0.004 inches to about 0.006 inches.

6. The exfoliating brush head of claim 5, wherein the first bristles of the tufts include a material selected from a group consisting of PET, TPE, PBT, nylon and polyester.

7. The exfoliating brush head of claim 1, wherein the second bristles include a material selected from a group consisting of PET, TPE, PBT and polyester.

8. The exfoliating brush head of claim 1, wherein the second bristles vary in height.

9. The exfoliating brush head of claim 1, wherein the tufts of the second group are configured so as to be deflected approximately 0.60 inches (15.240 millimeters) when a force of about 19 grams is applied thereto.

10. The exfoliating brush head of claim 1, wherein the tufts of the second group are formed by about 12-24 second bristles.

11. The exfoliating brush head of claim 1, wherein the tufts of the second group are formed by less than about 24 second bristles and the tufts of the first group are formed by more than about 120 first bristles.

12. The exfoliating brush head of claim 1, wherein each second bristle has a diameter in the range between about 0.012 inches and about 0.020 inches.

13. The exfoliating brush head of claim 12, wherein each first bristle has a diameter of about 0.004-0.006 inches and a height of about 0.360-0.400 inches, and wherein the tufts of the first group are formed by about 120-160 first bristles.

14. The exfoliating brush head of claim 1, wherein each second bristle has a diameter of about 0.012-0.020 inches, and wherein the tufts of the second group are formed by about 12-24 second bristles.

15. An exfoliating brush head for treating a patient's epidermis, comprising:

a brush body configured to be mountable to a drive system configurable to impart oscillating movement to the brush body;

a first group of tufts, each tuft comprising a plurality of first bristles outwardly extending from the brush body; and a second group of tufts configured to exfoliate a partially keratinized area of skin, each tuft comprising a plurality of second bristles outwardly extending from the brush body, wherein each bristle of the tufts of the second group of tufts extends from the brush body between about 0.225 inches to about 0.325 inches and has a diameter greater than about 0.008 inches, and wherein the tufts of the second group are formed by less than about 24 second bristles;

wherein the tufts of the second group of tufts are stiffer than the tufts of the first group.

16. The exfoliating brush head of claim 15, wherein the tufts of the first group are formed by more than about 120 first bristles.

17. The exfoliating brush head of claim 15, wherein the motion imparted to the brush body is oscillatory with an amplitude of about 8 degrees to 12 degrees and a frequency of about 94 Hz to 106 Hz.

18. The exfoliating brush head of claim 15, wherein the tufts of the second group include about 12-24 second bristles.

19. The exfoliating brush head of claim 18, wherein the tufts of the first group include about 120-160 first bristles.

20. The exfoliating brush head of claim 19, wherein the first bristles have a diameter of about 0.004-0.006 inches and a height of about 0.360-0.400 inches.

21. An exfoliating brush head for treating a patient's epidermis, comprising:

a brush body configured to be mountable to a drive system configurable to impart motion to the brush body;

a first group of tufts, each tuft comprising a plurality of first bristles outwardly extending from the brush body, wherein each first bristle has a diameter of about 0.004-0.006 inches and a height between about 0.360 to about 0.400 inches; and a second group of tufts, each tuft comprising a plurality of second bristles outwardly extending from the brush body, each second bristle has a diameter greater than 0.008 inches and a height between about 0.225 to about 0.325 inches.

22. The exfoliating brush head of claim 21, wherein the tufts of the first group are formed by more than 120 first bristles, and wherein the tufts of the second group are formed by less than 24 second bristles.

* * * * *